(12) United States Patent
Scozzesi

(10) Patent No.: US 9,045,534 B2
(45) Date of Patent: Jun. 2, 2015

(54) HMGB1 SPECIFIC MONOCLONAL ANTIBODIES

(75) Inventor: Cristina Scozzesi, Milan (IT)

(73) Assignee: Dia.Pro Diagnostic Bioprobes S.R.L., Milan (IT)

( * ) Notice: Subject to any disclaimer, the term of this patent is extended or adjusted under 35 U.S.C. 154(b) by 0 days.

(21) Appl. No.: 14/110,208

(22) PCT Filed: Apr. 5, 2011

(86) PCT No.: PCT/EP2011/055274
§ 371 (c)(1),
(2), (4) Date: Oct. 7, 2013

(87) PCT Pub. No.: WO2012/136250
PCT Pub. Date: Oct. 11, 2012

(65) Prior Publication Data
US 2014/0030271 A1    Jan. 30, 2014

(51) Int. Cl.
| | | |
|---|---|---|
| *A61K 39/395* | (2006.01) | |
| *C07K 16/28* | (2006.01) | |
| *C07K 16/18* | (2006.01) | |
| *C07K 16/24* | (2006.01) | |
| *A61K 39/00* | (2006.01) | |

(52) U.S. Cl.
CPC ........... *C07K 16/18* (2013.01); *A61K 2039/505* (2013.01); *C07K 16/24* (2013.01)

(58) Field of Classification Search
None
See application file for complete search history.

(56) References Cited

FOREIGN PATENT DOCUMENTS

| | | |
|---|---|---|
| EP | 2105447 A1 | 9/2009 |
| WO | WO2006138429 A2 | 12/2006 |

OTHER PUBLICATIONS

Yamada et al., "High Mobility Group Protein 1 (HMGB1) Quantified by ELISA with a Monoclonal Antibody That Does Not Cross-React with HMGB2," Clinical Chemistry 49(9):1535-1537 (2003).
Wu et al., "HMGB1 Contributes to Kidney Ischemia Reperfusion Injury," J Am Soc Nephrol 21(11):1878-1890 (2010).
Li et al., "Neutralization of the extracellular HMGB1 released by ischaemic-damaged renal cells protects against renal ischaemia-reperfusion injury," Nephrol Dial Transplant 26(2):469-478 (2011).
Watanabe et al., "The Role of HMGB-1 on the Development of Necrosis During Hepatic Ischemia and Hepatic Ischemia/Reperfusion Injury in Mice," The Journal of Surgical Research 124(1):59-66 (2005).
PCT International Search Report and Written Opinion for PCT/EP2011/055274, dated Oct. 10, 2011.

*Primary Examiner* — Phillip Gambel
(74) *Attorney, Agent, or Firm* — LeClairRyan, a Professional Corporation

(57) ABSTRACT

The present invention concerns monoclonal antibodies specifically binding the human HMGB1 protein and further HMGB1 proteins of mammalian origin and also concerns fragments thereof, nucleic acids encoding such antibodies or fragments thereof, as well as vectors, cells, and compositions comprising the antibodies or nucleic acids, and uses thereof.

7 Claims, 5 Drawing Sheets

HMGB1 SPECIFIC MONOCLONAL ANTIBODIES

This application is a national stage application under 35 U.S.C. §371 of PCT Application No. PCT/EP2011/055274, filed Apr. 5, 2011.

FIELD OF THE INVENTION

The present invention concerns monoclonal antibodies specifically binding the human HMGB1 protein and further HMGB1 proteins of mammalian origin and also concerns fragments thereof, nucleic acids encoding such antibodies or fragments thereof, as well as vectors, cells, and compositions comprising the antibodies or nucleic acids, and uses thereof.

STATE OF THE ART

High-mobility group protein B1 (HMGB1), also known as high-mobility group protein 1 (HMG-1) and amphoterin, is a protein that in humans is encoded by the HMGB1 gene (Ferrari et al., 1996).

Activated macrophages and monocytes secrete HMGB1 as a mediator of inflammation (Wang et al., 1999). Moreover, HMGB1 forms complexes with several other molecules or complex structures, including lipopolysaccharide (LPS), IL-1b, DNA, nucleosomes (Bianchi, 2009), and others. HMGB1, alone or in complex with partners, binds to TLR4 (Yang et al., 2010, Yang and Tracey, 2010) to RAGE (receptor for advanced glycation end-products), TLR2 and other receptors (Bianchi, 2009). This signaling results in recruitment of inflammatory cells to sites of tissue damage, dendritic cell activation, cytokine secretion (Bianchi and Manfredi, 2009). This positions HMGB1 at the intersection of sterile and infectious inflammatory responses. Moreover, HMGB1 also promotes the reconstruction of damaged tissue after trauma or infection (Bianchi and Manfredi, 2009). Individual monoclonal antibodies that neutralize HMGB1 can confer protection against damage and tissue injury during arthritis, colitis, ischemia, sepsis, endotoxemia, and systemic lupus erythematosus, but not necessarily against all the conditions at the same time, and not necessarily with the same profile of safety and lack of unwanted effects. The need and importance is therefore increasingly felt for the identification of a monoclonal antibody not only specific for HMGB1, but actually specific to well-determined surfaces on the protein, giving it the ability to interfere with the binding of HMGB1 to a subset of its partners.

It is therefore object of the present invention the development of a novel monoclonal antibody specific for HMGB1, and in particular capable of interfering with its chemoattractant activities towards inflammatory cells.

SUMMARY OF THE INVENTION

The present invention concerns a hybridoma which was deposited on the 22 Dec. 2010, under deposit accession number PD 10002, with the International Deposit Authority for cell lines and hybridomas "Interlab Cell Line Collection" (ICLC), which is a Core Facility of the Istituto Nazionale per la Ricerca sul Cancro in Genoa (Italy).

The hybridoma generated according to the present invention (HG-HMGB1) produces a mouse anti-HMGB1 monoclonal antibody (mAb) also defined as DPH1.1.

A further aspect of the present invention is a mouse (murine) anti-HMGB1 monoclonal antibody produced from the HG-HMGB1 hybridoma, or fragments and derivatives thereof.

The present invention also provides the sequence of light and heavy chains of the murine anti-HMGB1 monoclonal antibody.

A still further aspect of the present invention is a cell or vector comprising the murine anti-HMGB1 monoclonal antibody produced from the HG-HMGB1 hybridoma.

The variable region of the heavy chain of the murine anti-HMGB1 monoclonal antibody according to the present invention has a nucleotide sequence which corresponds to SEQ ID NO. 2 and an amino acid sequence which corresponds to SEQ ID NO.4.

The variable domain of the light chain of the murine anti-HMGB1 monoclonal antibody according to the present invention, has a nucleotide sequence which corresponds to SEQ ID NO. 3 and an amino acid sequence which corresponds to SEQ ID NO.5.

The present invention further relates to a murine anti-HMGB1 monoclonal antibody, for use as a diagnostic agent.

The present invention still further relates to a murine anti-HMGB1 monoclonal antibody, for use as a therapeutic agent.

A further aspect is a pharmaceutical composition comprising the murine anti-HMGB1 monoclonal antibody of the present invention as an active ingredient and a pharmaceutically bioactive excipient.

As will be further described in the detailed description of the invention, the pharmaceutical composition of the present invention has the advantages of being specific for the inhibition of the chemoattractant activities of HMGB1.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-6, wherein.

DETAILED DESCRIPTION OF THE INVENTION

Figure 1:
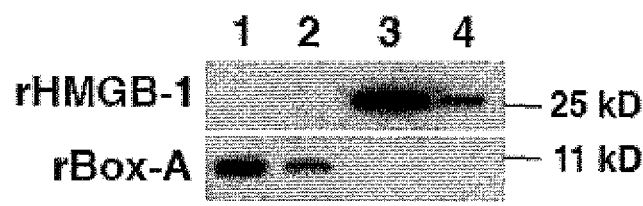
FIG. 1: shows representative western blots of 500 ng (lane 1) or 100 ng (lane 2) of the recombinant BoxA fragment of HMGB1 (negative control) and 500 ng (lane 3) or 100 ng (lane 4) of recombinant HMGB1 incubated with either the anti-HMGB1 mAb DPH1.1 (top panel) or a control anti-Box-A subunit Ab control (bottom panel), as described in Example 3.

The present invention concerns a hybridoma HB-HMGB1 which was internationally deposited on the 22 Dec. 2010, under deposit accession number PD 10002, with the International Deposit Authority for cell lines and hybridomas "Interlab Cell Line Collection" (ICLC), which is a Core Facility of the Istituto Nazionale per la Ricerca sul Cancro in Genoa (Italy).

The hybridoma generated according to the present invention (HG-HMGB1) produces a mouse (murine) anti-HMGB1 monoclonal antibody (mAb). The type of the immunized animal used in preparing the hybridoma can include a mouse, rat, hamster, rabbit, goat and horse, among which a mouse is preferably used. When a mouse is used, its strain is not particularly limited, but BALB/c mouse is preferably used.

A further aspect of the present invention is a mouse anti-HMGB1 monoclonal antibody produced from the HG-HMGB1 hybridoma, also defined as DPH1.1, or fragments and derivatives thereof.

The definition monoclonal antibody used herein includes fragments and derivatives of the monoclonal antibody, or any humanized anti-HMGB1 whose sequence is derived from DPH1.1 or from any antibody produced from the HG-HMGB1 hybridoma. Specifically, the fragments and derivatives of the monoclonal antibody are exemplified by Fab, Fab', F(ab)$_2$ and sFv fragment, and of sequences in the present antibody replacing sequences of antibodies of human origin, or from other mammalian species, not limited to IgG subclasses, but comprising IgM, IgE, IgD, IgE or the like.

The monoclonal antibody in the present embodiment can be obtained by immunizing an animal with HMGB1Ag as antigen by a known immunological method and then using cells of the immunized animal to prepare a hybridoma. DPH1.1 monoclonal antibodies of the present invention are produced by the hybridoma HB-HMGB1.

The present invention also provides the sequence of light and heavy chains of the murine anti-HMGB1 monoclonal antibody.

Each heavy chain has two regions, the constant region and the variable region. The constant region of the heavy chain corresponds to the *Mus musculus* immunoglobulin heavy chain complex (Igh) on chromosome 12 NCBI Reference Sequence: NG_005838.1

The variable region of the heavy chain of the murine anti-HMGB1 monoclonal antibody according to the present invention has a nucleotide sequence which corresponds to SEQ ID NO. 2 and an amino acid sequence which corresponds to SEQ ID NO.4.

The light chain has two successive domains: one constant domain and one variable domain. The constant domain corresponds to the *Mus musculus* immunoglobulin kappa chain complex (Igk) on chromosome 6 NCBI Reference Sequence: NG_005612.

The variable domain of the light chain of the murine anti-HMGB1 monoclonal antibody according to the present invention has a nucleotide sequence which corresponds to SEQ ID NO. 3 and an amino acid sequence which corresponds to SEQ ID NO.5.

For the purposes of the present invention, the HMGB1 monoclonal antibody (mAb) has a corresponding SEQ ID NO. as follows:

SEQ ID NO. 1 corresponds to the amino acid sequence of the 17-mer peptide P1 (KGKPDAAKKGVVKAEKS) derived from HMGB1;

SEQ ID NO. 2 corresponds to the nucleotide sequence of the cDNAs of the variable regions of the heavy chain of DPH1.1, [*mus musculus*];

CTGCTCGAGGAGTCTGGGGCAGAGCTTGTGAAGCCAGGGGCCTCAGTCAA

GTTGTCCTGCACAGCTTCTGGCTTCAACATTGAAGACACCTATGTGCACT

GGGTGAAGCAGAGGCCTGAACAGGGCCTGGAGTGGATTGGAAGGATTGAT

CCTGCGAATGGTAATAGTAAATATGACCCGAAGTTCCAGGGCAAGGCCAC

TCTAACAGCAGACACATTCTCCAACACAGCCTACCTGCAGCTCAGCAGCC

TGACATCTGAGGACACTGCCGTCTATTACTGTGCTGTAACTGGGACGGGG

GCTTTGG<u>ACTACTGGGGTCAAGGAACC</u> wherein: the "bold" sequence corresponds to the V heavy chain exon in the VHSM7 mouse germline genomic locus, the sequence in "italic" corresponds to the diversity region and the "underlined" sequence corresponds to the mouse germline IGHJ4 genomic locus.

The correspondence between the cDNA and the genomic loci is approximate, as expected, due to mutations introduced during B cell maturation.

SEQ ID NO. 3 corresponds to the nucleotide sequence of the cDNAs of the variable domains of the light chain of DPH1.1, [*mus musculus*];

TTGTTATTACTCGCTGCCCAACCAGCCATGGCCGAGCTCGTGTTGACGCA

GCCGCCATCGTCTCTGGCTGTGTCTGCAGGAGAAAAGGTCACTATGAGCT

GTAAGTCCAGTCAAAGTGTTTTATACAGTTCAAATCAGAAGAACTACTTG

GCCTGGTACCAGCAGAAACCAGGGCAGTCTCCTAAACTGCTGATCTACTG

GGCATCCACTAGGGAGTCTGGTGTCCCTGATCGCTTCACAGGCAGTGGAT

CTGGGACAGATTTTACTCTTAACATCACCAATGTACAACCTGACGACCTG

GCAGTTTATTACTGTCATCAATACCTCTCCTCGGTCACGTTCGGTGCTGG

GACCAAGCTGGAACTGAAACGGGCTGATGCTGCACC wherein: the "bold" sequence corresponds to the Igkv8-27 kappa light chain V exon in the mouse germline genomic locus, the sequence in "italic" corresponds to the mouse germline IGKJ5 genomic locus.

SEQ ID NO. 4 corresponds to the amino acid sequence of variable regions of the heavy chain of DPH1.1, [*mus musculus*];

LLEESGAELVKPGASVKLSCTASGFNIEDTYVHWVKQRPEQGLEWIGRID

PANGNSKYDPKFQGKATLTADTFSNTAYLQLSSLTSEDTAVYYCAVTGTG

ALDYWGQGT where the "bold" sequences correspond to the CDR regions 1, 2 and 3 respectively, as identified through the VBASE2 website (www.vbase2.org/).

SEQ ID NO. 5 corresponds to the amino acid sequence of variable domains of the light chain of DPH1.1, [*mus musculus*];

ELVLTQPPSSLAVSAGEKVTMSCKSSQSVLYSSNQKNYLAWYQQKPGQS

PKLLIYWASTRESGVPDRFTGSGSGTDFTLNITNVQPDDLAVYYCHQYLS

SVTFGAGTKLELKRADAA where the "bold" sequences correspond to the CDR regions 1, 2 and 3 respectively, as identified through the VBASE2 website (www.vbase2.org/).

The murine anti-HMGB1 monoclonal antibody according to the present invention is specific for a known epitope of HMGB1, represented by the sequence KGKPDAAKKGVV-KAEKS that is identical in mouse, human and most other mammals, and shows minimal cross-reactivity with other proteins, including HMGB2 which is 80% identical in sequence to HMGB1. Specificity of the anti-HMGB1 mAb has been in fact seen with respect to, but is not limited to the following mammalian HMGB1 genes:

*Homo sapiens*, where HMGB1 has the following Reference Sequences (Ref Seq): NM_002128.4→NP_002119.1;
*Mus musculus* HMGB1: NM_010439.3→NP_034569.1;
*Rattus norvegicus* HMGB1 NM_012963.2→NP_037095.1;
*Bos taurus* HMGB1: NM_176612.1→NP_788785.1;
*Equus caballus* HMGB1: NM_001081835.1→NP_001075304.1

It is therefore an advantage of the murine anti-HMGB1 monoclonal antibody according to the present invention to be specific for a epitope of HMGB1 that is identical in many mammalian species.

A further advantage of the murine anti-HMGB1 monoclonal antibody according to the present invention is that it shows minimal cross-reactivity with other proteins, including HMGB2 which is 80% identical in sequence to HMGB1.

A still further advantage of the murine anti-HMGB1 monoclonal antibody DPH1.1 is that of being able to block HMGB1-elicited cell migration. This unexpected advantage is important since the recruitment of inflammatory cells to the site of tissue damage is an important element in the causation and continuation of acute and chronic inflammation.

It is shown in the example that HMGB1 release from hepatocytes contributes to recruit PMNs into the liver, and that neutralization of HMGB1 with DPH1.1 mAb reduces the recruitment of PMNs.

The DPH1.1 mAb according to the present invention advantageously blocks cell migration, and in particular has been seen to reduce polymorphonuclear leukocytes recruitment in vivo, as well as in vitro. Accordingly, the severity of hepatitis (as measured by sALT levels in the blood) is reduced.

A still further aspect of the present invention is a cell or a vector comprising the murine anti-HMGB1 monoclonal antibody produced from the HG-HMGB1 hybridoma.

The present invention further relates to a monoclonal antibody, for use as a diagnostic agent.

The principal diagnostic agents are X-ray-contrast preparations, radioactive isotopes, and dyes. A diagnostic agent can be used for making images of many different body parts.

The monoclonal antibody of the present invention can be used in immunoassays for detection and/or quantification of HMGB1 since the monoclonal antibody has the advantage of recognizing an epitope that is identical in mouse, human and other mammals, for example in a sample suspected of containing HMGB1 protein, either unmodified or post-translationally modified. Such immunoassay can be used in clinical diagnosis of pathologies associated with trauma, tissue damage, acute and chronic inflammation, autoimmune diseases including lupus and in the screening of blood products.

The present invention still further relates to a monoclonal antibody, for use as a therapeutic agent.

Targeted therapies are the focus of much research in medicine. Biological therapies that target pathology-associated antigens give hope for improvement of survival in many types of illnesses. Tumor specific antigens have been for example widely studied in the hope for cancer treatment.

The mAb according to the present invention is useful in the treatment of pathologies including but not limited to hepatitis, trauma, infection, arthritis, ischemia, organ transplantation, in which the inhibition of the chemoattractant activities of HMGB1 is implicated.

A further aspect is a pharmaceutical composition comprising the monoclonal antibody of the present invention as an active ingredient and a pharmaceutically bioactive excipient.

The pharmaceutical composition of the present invention has the advantages of being specific for the inhibition of the chemoattractant activities of HMGB1.

EXAMPLES

Example 1

Preparation of Monoclonal Antibody

Immunization of Mouse and Hybridoma Generation

The mouse monoclonal IgG1 DPH1.1 Ab specific for mouse HMGB1 was generated by injecting C57BL/6 6-week-old female mice at two-week intervals with three subcutaneous doses (0.2 mg/mouse) of the 17-mer peptide P1 (KGKPDAAKKGVVKAEKS) (SEQ ID NO.1) derived from HMGB1.

Hybridomas according to the present invention (HG-HMGB1) were generated from splenocytes and from a hypoxanthine-aminopterin-thymine (HAT) sensitive myeloma P3/NSI/1-A04-1 cells by standard techniques and tested by ELISA against the immunogen.

Example 2

Preparation of Monoclonal Antibody

Culture of the Hybridoma

Hybridoma colonies are grown in RPMI 1640 medium additioned with 15% FCS and HAT for 10 days, and manually selected after microscopic analysis.

HMGB1 positivity of the colonies was monitored by ELISA analysis of the colony supernatant.

Positive colonies were transferred to larger wells and subjected to 2 rounds of limiting dilution.

Stable and immortalized DPH1.1 hybridoma clones were obtained.

The DPH1.1 clone was grown for 3 months in a disposable bioreactor for efficient protein expression, using standard techniques, supernatant was collected.

Purification of the supernatant to obtain the monoclonal antibody was performed on a PROT A chromatographic column.

The monoclonal antibody anti HMGB1 was therefore obtained with a percentage of purity of 95%. The monoclonal antibody anti HMGB1 was further purified to 100% purity with further chromatographic purification passages.

Example 3

Figure 2:
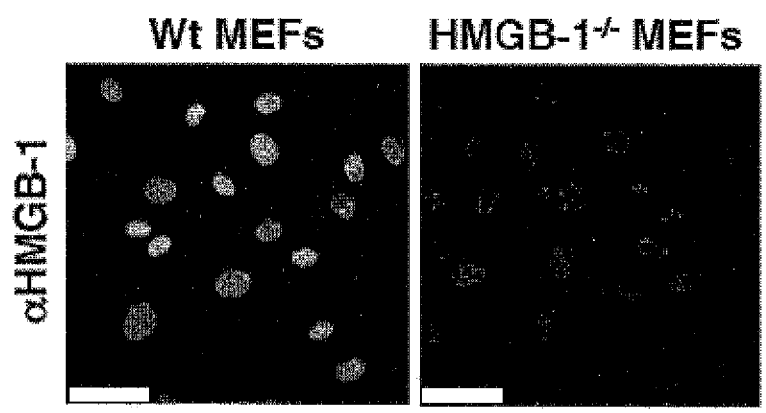
FIG. 2: shows representative micrographs of mouse embryonic fibroblasts (MEFs) derived from either wild type (wt) mice or Hmgb1−/− mice that were stained by immunofluorescence with the anti-HMGB1 mAb DPH1.1. Scale bar represents 20 μm, as described in Example 3.

Anti-HMGB1 Ab (DPH1.1 mAb) Characterization and Specificity Testing by Immunofluorescence Specificity of DPH1.1 mAb was monitored by both Western blot analysis (FIG. 1) and by immunofluorescence (FIG. 2).
Anti-HMGB-1 Ab (DPH1.1 Ab) Characterization and Specificity Testing by Western Blot
Western blots of the recombinant BoxA domain of HMGB1 (negative control) incubated with either the anti-HMGB-1 mAb DPH1.1 or a control anti-BoxA mAb control were performed.
Briefly, 500 ng or 100 ng of recombinant HMGB1 and the (negative control) recombinant BoxA domain of HMGB1 (HMGBiotech, Milan, Italy) were separated by gel electrophoresis and transferred onto membranes as described (Scaffidi et al., 2002).
Results
As can be seen in FIG. 1, the anti-HMGB1 mAb DPH1.1 according to the present invention specifically binds the recombinant HMGB1, but not the BoxA domain.
Immunofluorescence
DPH1.1 mAb, anti-BoxA mAb (HMGBiotech, Milan, Italy) and goat anti-mouse IgG1 Ab (BD PharMingen) were applied at 1 µg/ml dilution. Immunofluorescence was performed as described (Scaffidi et al., 2002) on mouse embryonic fibroblasts (MEFs) derived from either wild type mice or Hmgb1−/− mice. DPH1.1 mAb and ALEXAFLUOR® 633-labelled goat anti-mouse IgG1 Ab (BD PharMingen) were applied at a 50 µg/ml dilution.
Results
As can be seen in FIG. 2: only mouse embryonic fibroblasts derived from Hmgb1−/− mice were stained with the anti-HMGB1 monoclonal antibody DPH1.1.

Example 4

Transmigration Assay

Figure 3:
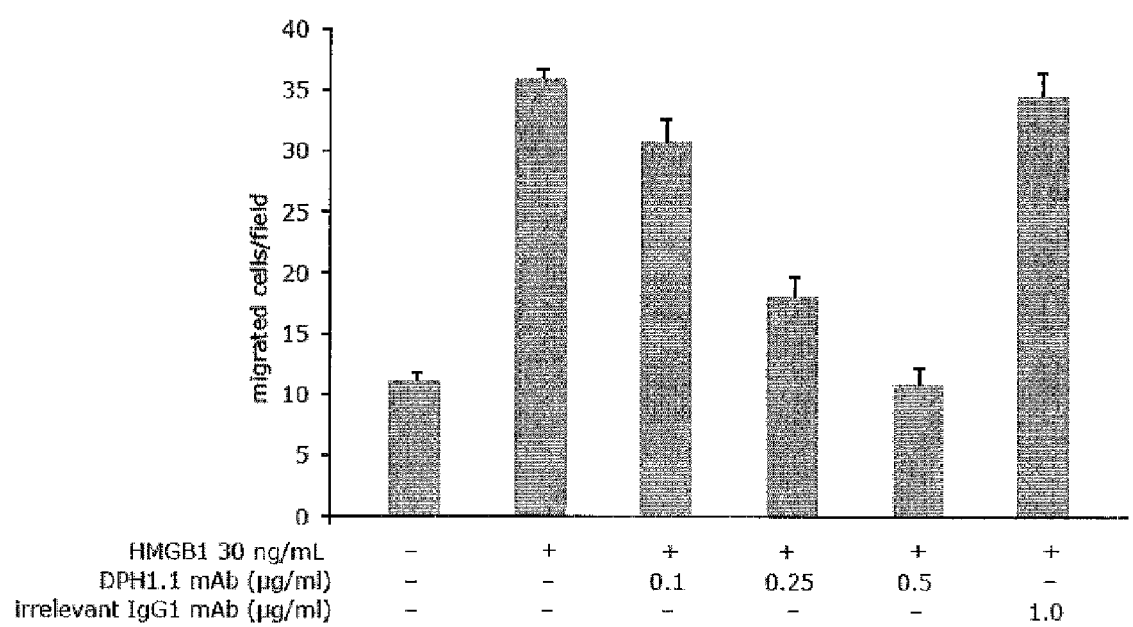
FIG. 3: shows migration of 3T3 cells towards HMGB1 in the presence of the indicated concentrations of the anti-HMGB1 mAb, examined using a modified Boyden chamber assay. Each bar represents the mean number of migrated cells±standard deviation of triplicate samples, as described in Example 4.

The in vitro activity of DPH1.1 mAb was monitored in trans-well migration assays as described (Palumbo et al., 2009).
Briefly, recombinant HMGB1 was added to the lower chamber at the concentration of 30 ng/ml. Increasing concentrations of DPH1.1 mAb (or of an irrelevant isotype-matched mAb) were added to fifty thousand 3T3 cells. Cell migration was assessed by a modified Boyden chamber assay.
Boyden chambers were incubated at 37° C. in 5% $CO_2$ for 3 hrs. Cells remaining on the upper section of the filters were removed mechanically. Cells that migrated to the lower section of the filters were fixed with ethanol, stained with Giemsa (Sigma-Aldrich), and counted in 10 random fields/filter. Each assay was performed in duplicate and repeated at least three times, independently.
Results:
As can be seen in FIG. 3, increasing concentrations of DPH1.1 mAb unexpectedly inhibit cell migration. These results show the surprising effect of the DPH1.1 mAb, which blocks HMGB1 elicited cell migration.

Example 5

In Vivo Experiments

Inflammatory Cell Recruitment

Figure 4:
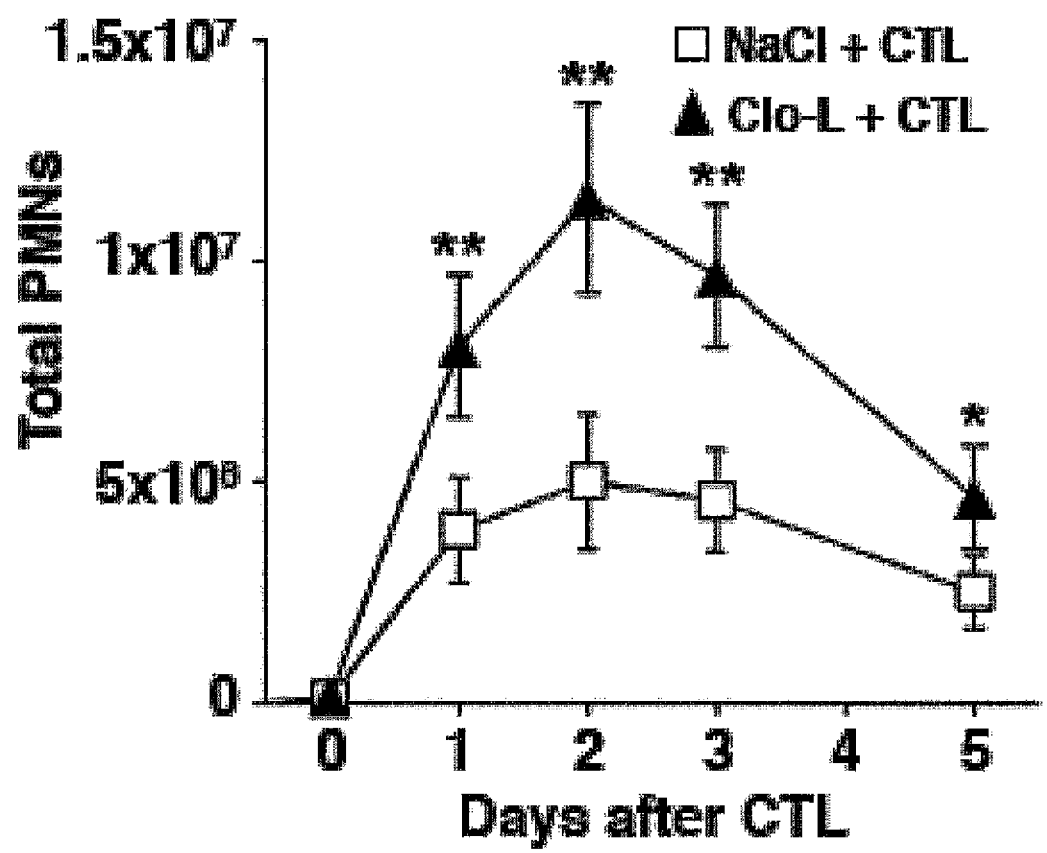
FIG. 4: shows the results of the in vivo experiments of inflammatory cell recruitment, as described in Example 5.
Figure 5A:
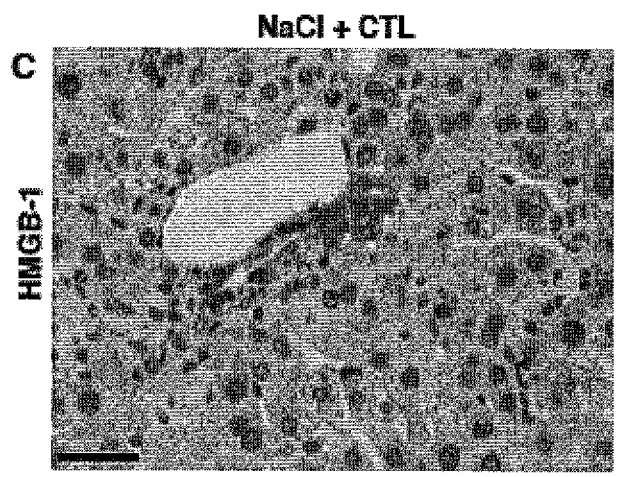
FIG. 5A and FIG. 5B: show the results of the representative immunohistochemical micrographs of control (FIG. 5A) or Clo-L-treated (FIG. 5B) livers from HBV transgenic mice, two days after intravenous injection of 107 HBV-specific CTLs as described in Example 5. In particular: HMGB1 staining in brown. Note the nuclear-to-cytoplasm translocation of HMGB1 in hepatocytes surrounded by PMNs (arrowhead). Scale bar represents 150 μm. The experiment was replicated in triplicate. Error bars show standard deviation. * $p<0.05$ and ** $p<0.01$ between DPH1.1 and isotype-matched irrelevant antibody (ANOVA plus t-test with Bonferroni correction).
Figure 5B:
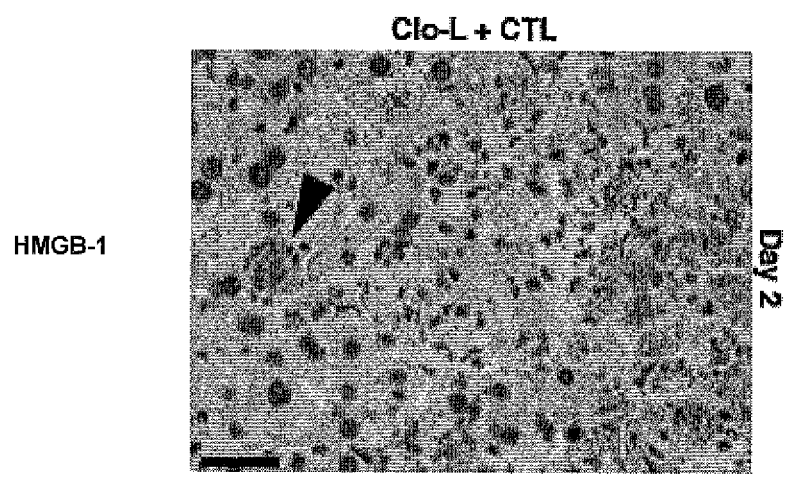
Figure 6A:
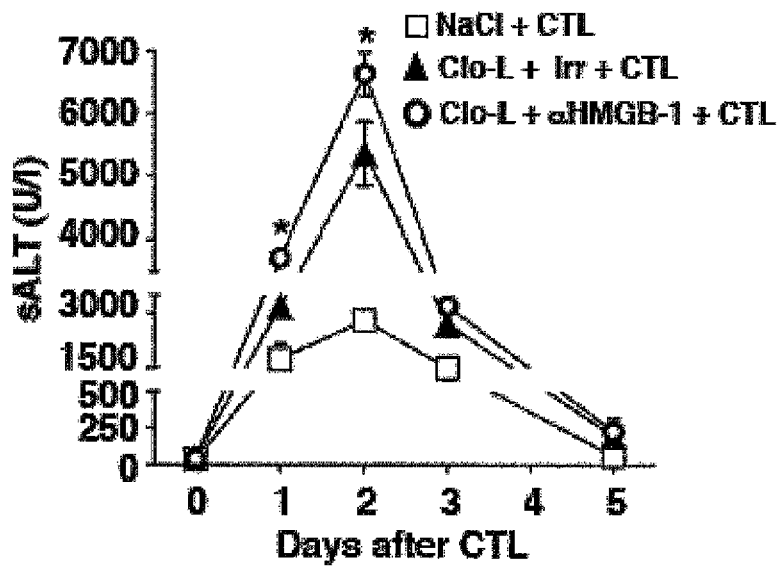
FIG. 6A.
Figure 6B:
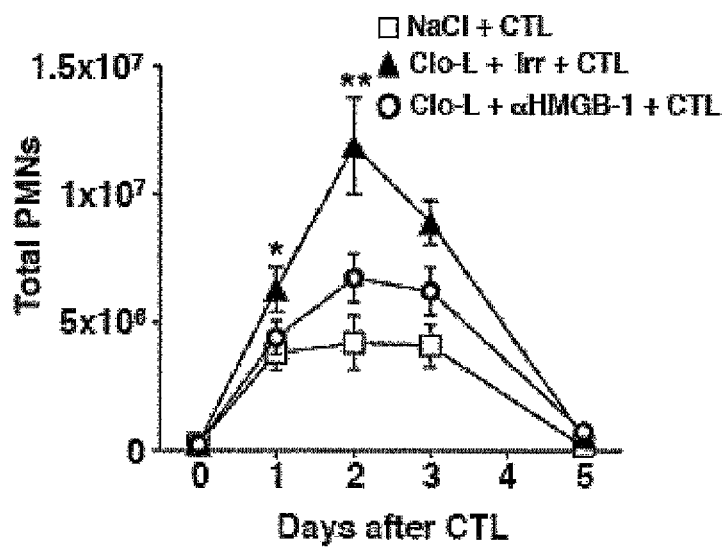
FIG. 6B: are representative graphs of the results of the in vivo experiments as described in Example 5. In particular, sALT levels in the blood (FIG. 6A) and absolute number of Gr-1$^{high}$ CD11b$^+$ neutrophils (PMNs) recovered from the livers (FIG. 6B) of 6 HBV transgenic mice that received NaCl (white squares), Clo-L and irrelevant (Irr) IgG1 mAb (black triangles) or Clo-L and the anti-HMGB1 mAb DPH1.1 (black circles) along with the intravenous injection of 10$^7$ HBV-specific CTLs. Error bars show standard deviation. * p<0.05 and ** p<0.01 between DPH1.1 and isotype-matched irrelevant antibody (ANOVA plus t-test with Bonferroni correction).

We had previously shown that inflammatory cells are recruited into the liver by the release of HMGB1 protein (Sitia et al, 1997).
Recruitment of inflammatory cells can be amplified by removal of Kupffer cells (KCs) from the liver, which can be obtained by treatment of the mice with clodronate (Clo-L).
In order to amplify the effect of HMGB1, we removed Kupffer cells (KCs) from HBV transgenic mice, and we injected them with CD8 T cells from mice immunized against HBV (this causes acute hepatitis in the mice). In these mice, we found far larger numbers intrahepatic PMNs than in mice not treated with clodronate (FIG. 4). We also found many more hepatocytes expressing cytoplasmic HMGB1 juxtaposed to or surrounded by polymorphonucleate cells (PMNs) in comparison to mice that were not treated with clodronate (FIG. 5A and FIG. 5B).
Results
Removal of KCs promoted accumulation of cytoplasmic HMGB1 in hepatocytes and intrahepatic PMN infiltration over what normally seen in mice where KCs were not removed.
Effect of DPH1.1 Administration
We tested the effect of administration of the DPH1.1 mAb.
The livers of mice treated with DPH1.1 mAb contained many more hepatocytes expressing cytoplasmic HMGB1 (not shown), higher sALT values (FIG. 6A), but reduced numbers infiltrating PMNs (FIG. 6B).
Results
These results show that HMGB1 release from hepatocytes contributes to recruit PMNs into the liver, and that neutralization of HMGB1 with DPH1.1 reduces the recruitment of PMNs and hepatitis.
The DPH1.1 mAb according to the present invention blocks cell migration towards HMGB1 in vivo, as well as in vitro.
Methods:
Mice. HBV replication-competent transgenic mouse (lineage 1.3.32) have been previously described (Guidotti et al., 1995). Lineage 1.3.32 (inbred C57BL/6, H-2b) was crossed with B10.D2 mice (H-2d) to produce H-2bxd F1 hybrids prior to injection of H-2d-restricted hepatitis B surface antigen (HBsAg)-specific CD8 T cell lines. C57BL/6 and B6.PL-Thy1a/CyJ (Thy-1.1) mice were purchased from The Scripps Research Institute breeding colony or from Charles River Laboratories (Calco, Italy). Bone marrow chimeric phosphoglycerate kinase (PGK)-GFP mice replicating HBV were created by transplanting BM cells derived from PGK-GFP (H-2bxd F1 hybrids, a kind gift of Michele De Palma, San Raffaele Scientific Institute, Milan, Italy) into irradiated 1.3.32 HBV mice. Thy-1.1 mice were crossed once with B10.D2 mice prior to immunization with plasmid DNA- and vaccinia virus-encoding HBsAg as previously described (lannacone et al., 2005). In all experiments mice were matched for age (8 weeks), sex (males) and, in case of lineage 1.3.32, for serum hepatitis B e antigen (HBeAg) levels before experimental manipulation. All animals were housed in pathogen-free rooms under strict barrier conditions. These studies were approved by the Animal Review Board of the San Raffaele Scientific Institute.

Injection of HBV-specific CD8 T cell lines. HBV-specific CD8 T cell lines were derived from spleen cells of immunized nontransgenic Thy-1.1×B10.D2 male mice as described (Iannacone et al., 2005). After 3 weeks of in vitro stimulation, the cells were tested for antigen specificity by flow cytometry. CD8+ cells that were over 95% specific for the immunodominant peptide epitope Env 28-39 of HBsAg (Ando et al., 1994) were injected intravenously at different doses (0.5×10$^7$ cells/mouse, 10$^7$ cells/mouse or 5×10$^7$ cells/mouse) into 1.3.32 mice. One, 2, 3, or 5 days later mice were killed and their livers were perfused and harvested for histological and flow cytometry analyses, or they were snap-frozen in liquid nitrogen and stored at −80° C. for subsequent molecular analyses.

Depletion of KCs. KC depletion was achieved by intravenous injection of 200 µl of clodronate-containing liposomes (Clo-L, a gift of Roche Diagnostics GmbH, Mannheim, Germany) 3 days before CD8 T cell transfer.

From the above description and the above-noted examples, the advantage attained by the product described and obtained according to the present invention are apparent.

REFERENCES

Ando K, Guidotti L G, Cerny A, Ishikawa T, Chisari F V (1994), CTL access to tissue antigen is restricted in vivo. J. Immunol. 1994 Jul. 15; 153(2):482-8.

Bianchi M E (2009) HMGB1 loves company. J Leukoc Biol 86: 573-6

Bianchi M E and Manfredi A A. (2009) Immunology. Dangers in and out. Science 323: 1683-4

Ferrari S, Finelli P, Rocchi M, Bianchi M E (July 1996). "The active gene that encodes human high mobility group 1 protein (HMG1) contains introns and maps to chromosome 13". Genomics 35 (2): 367-71.

Guidotti, L. G., B. Matzke, H. Schaller, and F. V. Chisari. 1995. High-level hepatitis B virus replication in transgenic mice. J Virol 69:6158-6169

Iannacone, M., G. Sitia, M. Isogawa, P. Marchese, M. G. Castro, P. R. Lowenstein, F. V. Chisari, Z. M. Ruggeri, and L. G. Guidotti. 2005. Platelets mediate cytotoxic T lymphocyteinduced liver damage. Nature medicine 11:1167-1169

Palumbo, R., F. De Marchis, T. Pusterla, A. Conti, M. Alessio, and M. E. Bianchi. 2009. "Src family kinases are necessary for cell migration induced by extracellular HMGB1." J Leukoc Biol 86:617-623.

Scaffidi, P., T. Misteli, and M. E. Bianchi. 2002. "Release of chromatin protein HMGB1 by necrotic cells triggers inflammation." Nature 418:191-195.

Sitia G, Iannacone M, Müller S, Bianchi M E and Guidotti L G (2007) Treatment with HMGB1 inhibitors diminishes CTL-induced liver disease in HBV transgenic mice. J Leukoc Biol 81: 100-7

Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J (July 1999). "HMG-1 as a late mediator of endotoxin lethality in mice". Science 285 (5425): 248-51.

Yang H, Hreggvidsdottir H S, Palmblad K, Wang H, Ochani M, Li J, Lu B, Chavan S, Rosas-Ballina M, Al-Abed Y, Akira S, Bierhaus A, Erlandsson-Harris H, Andersson U, Tracey K J (June 2010). "A critical cysteine is required for HMGB1 binding to Toll-like receptor 4 and activation of macrophage cytokine release". Proc. Natl. Acad. Sci. U.S.A. 107 (26): 11942-7.

Yang H, Tracey K J (2010). "Targeting HMGB1 in inflammation". Biochim. Biophys. Acta 1799 (1-2): 149-56.

---

The invention claimed is:

1. A hybridoma which is deposited under deposit Accession No. PD 10002, with International Deposit Authority Interlab Cell Line Collection, Genoa Italy.

2. A murine anti-HMGB1 monoclonal antibody produced by the hybridoma according to claim 1, or fragments of the anti-HMGB1 monoclonal antibody selected from the group consisting of Fab, Fab', F(ab)2, and sFv and humanized derivatives of anti-HMGB1 whose sequence is derived from DPH1.1.

3. The murine anti-HMGB1 monoclonal antibody according to claim 2, wherein the variable region of the heavy chain has a nucleotide sequence which corresponds to SEQ ID NO. 2 and an amino acid sequence which corresponds to SEQ ID NO.4.

4. The murine anti-HMGB1 monoclonal antibody according to claim 2, wherein the variable domain of the light chain has a nucleotide sequence which corresponds to SEQ ID NO. 3 and an amino acid sequence which corresponds to SEQ ID NO.5.

5. A method of detecting and/or quantifying HMGB1 in a sample, said method comprising:

contacting a biological sample with the murine anti-HMGB1 monoclonal antibody according to claim 2, wherein the murine anti-HMGB1 monoclonal antibody binds to HMGB1 in the sample and detecting and/or quantifying the murine anti-HMGB1 monoclonal antibody bound to the HMGB1 to detect and/or quantify the HMGB1 in said sample.

6. A method of blocking HMGB1-elicited cell migration comprising:

administering in a mammal the murine anti-HMGB1 monoclonal antibody according to claim 2, to block HMGB1-elicited cell migration in the mammal.

7. A pharmaceutical composition comprising the monoclonal antibody according to claim 4 as an active ingredient and a pharmaceutically bioactive excipient.

* * * * *

SEQUENCE LISTING

```
<160> NUMBER OF SEQ ID NOS: 5

<210> SEQ ID NO 1
<211> LENGTH: 17
<212> TYPE: PRT
<213> ORGANISM: Mus musculus

<400> SEQUENCE: 1

Lys Gly Lys Pro Asp Ala Ala Lys Lys Gly Val Val Lys Ala Glu Lys
1               5                   10                  15

Ser

<210> SEQ ID NO 2
<211> LENGTH: 327
<212> TYPE: DNA
<213> ORGANISM: Mus musculus

<400> SEQUENCE: 2
ctgctcgagg agtctggggc agagcttgtg aagccagggg cctcagtcaa gttgtcctgc      60
acagcttctg gcttcaacat tgaagacacc tatgtgcact gggtgaagca gaggcctgaa     120
cagggcctgg agtggattgg aaggattgat cctgcgaatg gtaatagtaa atatgacccg     180
aagttccagg gcaaggccac tctaacagca gacacattct ccaacacagc ctacctgcag     240
ctcagcagcc tgacatctga ggacactgcc gtctattact gtgctgtaac tgggacgggg     300
gctttggact actggggtca aggaacc                                         327
```

<210> SEQ ID NO 3
<211> LENGTH: 386
<212> TYPE: DNA
<213> ORGANISM: Mus musculus

<400> SEQUENCE: 3

```
ttgttattac tcgctgccca accagccatg gccgagctcg tgttgacgca gccgccatcg      60
tctctggctg tgtctgcagg agaaaaggtc actatgagct gtaagtccag tcaaagtgtt     120
ttatacagtt caaatcagaa gaactacttg gcctggtacc agcagaaacc agggcagtct     180
cctaaactgc tgatctactg gcatccact  agggagtctg gtgtccctga tcgcttcaca     240
ggcagtggat ctgggacaga ttttactctt aacatcacca atgtacaacc tgacgacctg     300
gcagtttatt actgtcatca atacctctcc tcggtcacgt tcggtgctgg gaccaagctg     360
gaactgaaac gggctgatgc tgcacc                                          386
```

<210> SEQ ID NO 4
<211> LENGTH: 109
<212> TYPE: PRT
<213> ORGANISM: Mus musculus

<400> SEQUENCE: 4

```
Leu Leu Glu Glu Ser Gly Ala Glu Leu Val Lys Pro Gly Ala Ser Val
1               5                   10                  15

Lys Leu Ser Cys Thr Ala Ser Gly Phe Asn Ile Glu Asp Thr Tyr Val
            20                  25                  30

His Trp Val Lys Gln Arg Pro Glu Gln Gly Leu Glu Trp Ile Gly Arg
        35                  40                  45

Ile Asp Pro Ala Asn Gly Asn Ser Lys Tyr Asp Pro Lys Phe Gln Gly
    50                  55                  60

Lys Ala Thr Leu Thr Ala Asp Thr Phe Ser Asn Thr Ala Tyr Leu Gln
65                  70                  75                  80

Leu Ser Ser Leu Thr Ser Glu Asp Thr Ala Val Tyr Tyr Cys Ala Val
                85                  90                  95

Thr Gly Thr Gly Ala Leu Asp Tyr Trp Gly Gln Gly Thr
            100                 105
```

<210> SEQ ID NO 5
<211> LENGTH: 117
<212> TYPE: PRT
<213> ORGANISM: Mus musculus

<400> SEQUENCE: 5

```
Glu Leu Val Leu Thr Gln Pro Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Asn
65                  70                  75                  80

Ile Thr Asn Val Gln Pro Asp Asp Leu Ala Val Tyr Tyr Cys His Gln
                85                  90                  95
```

-continued

```
Tyr Leu Ser Ser Val Thr Phe Gly Ala Gly Thr Lys Leu Glu Leu Lys
            100             105             110

Arg Ala Asp Ala Ala
        115
```